(12) United States Patent
Tanaka

(10) Patent No.: US 11,751,768 B2
(45) Date of Patent: Sep. 12, 2023

(54) BIOLOGICAL DATA MEASURING DEVICE

(71) Applicant: TECHNO-COMMONS INC., Nagano (JP)

(72) Inventor: Akio Tanaka, Himeji (JP)

(73) Assignee: TECHNO-COMMONS, INC., Nagano (JP)

(*) Notice: Subject to any disclaimer, the term of this patent is extended or adjusted under 35 U.S.C. 154(b) by 409 days.

(21) Appl. No.: 16/958,917

(22) PCT Filed: Oct. 31, 2018

(86) PCT No.: PCT/JP2018/040460
§ 371 (c)(1),
(2) Date: Jun. 29, 2020

(87) PCT Pub. No.: WO2019/130797
PCT Pub. Date: Jul. 4, 2019

(65) Prior Publication Data
US 2020/0359906 A1 Nov. 19, 2020

(30) Foreign Application Priority Data
Dec. 28, 2017 (JP) ................................ 2017-253079

(51) Int. Cl.
*A61B 5/01* (2006.01)
*A61B 5/00* (2006.01)
(Continued)

(52) U.S. Cl.
CPC .............. *A61B 5/01* (2013.01); *A61B 5/0024* (2013.01); *A61B 5/6802* (2013.01);
(Continued)

(58) Field of Classification Search
CPC ....... A61B 5/0024; A61B 5/01; A61B 5/6802; A61B 5/6833; A61B 2560/0214;
(Continued)

(56) References Cited

U.S. PATENT DOCUMENTS

| | | | |
|---|---|---|---|
| 9,997,059 B2 | 6/2018 | Katsurai et al. | |
| 2005/0141591 A1* | 6/2005 | Sakano | G01K 15/00 374/E1.004 |
| 2011/0249701 A1* | 10/2011 | Bieberich | G01K 13/20 374/163 |
| 2012/0114013 A1* | 5/2012 | Tsuchida | G01K 13/20 374/185 |

(Continued)

FOREIGN PATENT DOCUMENTS

| | | |
|---|---|---|
| JP | S63-58223 A | 3/1988 |
| JP | 2009-222543 A | 10/2009 |

(Continued)

OTHER PUBLICATIONS

PCT/ISA/210, "International Search Report for International Application No. PCT/JP2018/040460," dated Jan. 29, 2019.

*Primary Examiner* — Orlando Bousono
(74) *Attorney, Agent, or Firm* — Manabu Kanesaka

(57) ABSTRACT

A biological data measurement device has patches. A patch to be mounted on the human body basically includes first and second heat insulators, first and second temperature measurement circuits, and a belt-shaped wiring film (bus wire). Therefore, the configuration is simple. For example, a thickness can be approximately several mm, and a weight can be approximately several grams. The patch is easily mounted on the human body, and is inexpensive. The patch is equipped with a selection circuit, and selectively outputs a temperature signal of a first thermometer and a temperature signal of a second thermometer at a predetermined timing. Accordingly, even in a case where the patches are mounted on a plurality of locations of the human body, the number of wires is settled by the number required for one patch. The number of wires can be significantly reduced, compared to the number of wires in the related art.

16 Claims, 19 Drawing Sheets

(51) Int. Cl.
*G01K 7/01* (2006.01)
*G01K 7/16* (2006.01)

(52) U.S. Cl.
CPC .............. *A61B 5/6833* (2013.01); *G01K 7/01* (2013.01); *G01K 7/16* (2013.01); *A61B 2560/0214* (2013.01); *A61B 2562/0271* (2013.01); *A61B 2562/182* (2013.01); *A61B 2562/22* (2013.01)

(58) Field of Classification Search
CPC ...... A61B 2562/0271; A61B 2562/182; A61B 2562/22; G01K 7/01; G01K 7/16; G01K 1/02; G01K 1/024; G01K 1/14; G01K 1/16; G01K 13/00; G01K 13/002; G01K 13/20
See application file for complete search history.

(56) References Cited

U.S. PATENT DOCUMENTS

| | | | |
|---|---|---|---|
| 2013/0010828 | A1* | 1/2013 | Bieberich .............. G01K 13/20 374/163 |
| 2016/0238463 | A1* | 8/2016 | Bieberich ................ G01K 7/22 |
| 2017/0276553 | A1* | 9/2017 | Nakagawa .............. G01K 13/20 |
| 2018/0028072 | A1* | 2/2018 | Shi ....................... A61B 5/6833 |
| 2018/0064348 | A1 | 3/2018 | Tsuchimoto |

FOREIGN PATENT DOCUMENTS

| | | |
|---|---|---|
| JP | 2016-115219 A | 6/2016 |
| WO | 2011/012386 A1 | 2/2011 |
| WO | 2013/140720 A1 | 9/2013 |
| WO | 2016/185905 A1 | 11/2016 |

\* cited by examiner

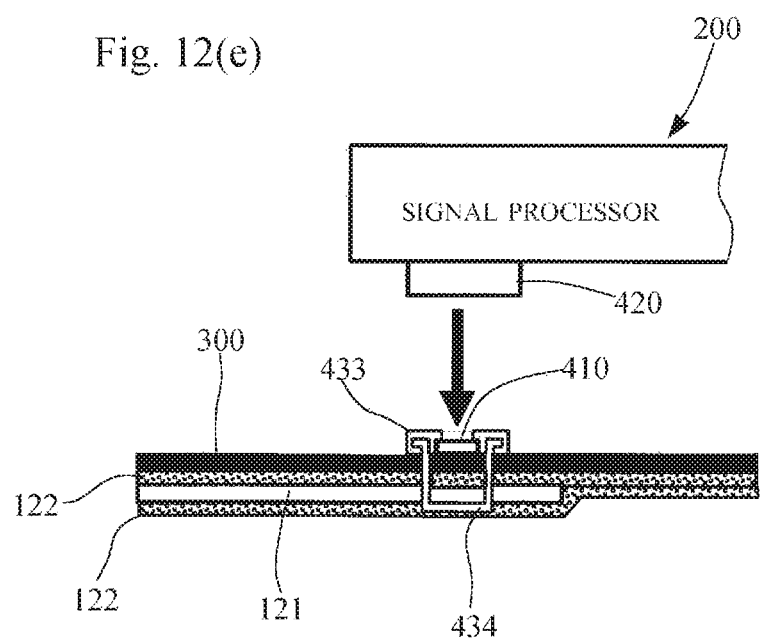

BIOLOGICAL DATA MEASURING DEVICE

RELATED APPLICATIONS

The present application is National Phase of International Application No. PCT/JP2018/040460 filed Oct. 31, 2018, and claims priority from Japanese Application No. 2017-253079 filed Dec. 28, 2017, the disclosure of which is hereby incorporated by reference herein in its entirety.

TECHNICAL FIELD

The present invention relates to a biological data measurement device attached to a body surface of a living body to measure biological data such as a body temperature, and more specifically relates to a biological data measurement device that particularly measures a core body temperature of a living body.

BACKGROUND ART

Currently, as a method for measuring a core body temperature by attaching a device to a body surface of a living body, for example, a Single Heat Flux (SHF) method, a Dual Heat Flux (DHF) method, and a Zero Heat Flux (ZHF) method are known.

As an example of the Single Heat Flux (SHF) method, FIG. 19 illustrates a configuration of FIGS. 2(a) and 2(b) disclosed in PTL 1. In the drawing, the reference numeral 2 represents a first probe, the reference numeral 6 represents a second probe, the reference numeral 4 represents a heat insulator, and the reference numeral 3 represents a body surface. The first probe 2 and the second probe 6 measure a heat flow (heat flux) substantially vertically generated from the body surface 3.

According to the SHF method, a heater is not required. Therefore, there is an advantage of low power consumption and a simplified configuration. However, there is a disadvantage in that a measurement time needs approximately 10 minutes. In addition, it is necessary to measure heat resistance inside the living body (internal heat resistance) in advance by using another method.

Next, as an example of the Dual Heat Flux (DHF) method, FIG. 20 illustrates a configuration of FIGS. 1(a) and 1(b) disclosed in PTL 2. In the drawing, the reference numerals 11 and 17 represent a pair of first temperature sensors, and the reference numerals 12 and 18 represent a pair of second temperature sensor. A core body temperature of the living body is measured, based on the heat flow measured by the pair of first temperature sensors 11 and 17 and the heat flow measured by the pair of first temperature sensors 12 and 18.

According to the DHF method, the core body temperature can be recognized without measuring the heat resistance inside the body by using another method. In addition, the heater is not required. Therefore, there is an advantage of low power consumption. However, the measurement time also needs approximately 10 minutes, and there is a disadvantage in that it is necessary to provide two pairs of temperature sensors.

In addition, as an example of the Zero Heat Flux (ZHF) method, FIG. 21 illustrates a configuration of FIG. disclosed in PTL 3. In the drawing, the reference numeral 140 represents a temperature sensor and the reference numeral 126 represents a heater. According to the ZHF method, the temperature sensor 140 attached to a skin surface is heated by the heater 126. When the temperature sensor 140 and the core body temperature reach equilibrium (approximately 3 minutes), the core body temperature is displayed on a display unit.

According to the ZHF method, there is an advantage in that the measurement time is relatively short and needs approximately 3 minutes. However, on the other hand, there is a disadvantage in that approximately 1 W (watt) is required for power consumption of the heater. In addition, in a case of the ZHF method, the power consumption of approximately 1 W is required. Consequently, the ZHF method is less likely to be applicable to a bandage-type sensor used by being attached to the body surface.

CITATION LIST

Patent Literature

[PTL 1] Pamphlet of International Publication WO2011/012386 (particularly FIGS. 2(a) and 2(b))
[PTL 2] JP-A-63-58223 (particularly FIGS. 1(a) and 1(b))
[PTL 3] US Patent Publication No. 2016/0238463 (particularly FIG. 6)

SUMMARY OF INVENTION

Technical Problem

According to any one of the methods, in a case where sensors are mounted on a plurality of locations in a human body in order to acquire a lot of (various items of) biological data, for example, when the number of wires per one sensor is denoted by m and the number of attachment locations is denoted by n, the number of wires to be laid around is m×n as a whole. Consequently, a wiring process is complicated. Moreover, for example, in a case where the biological data is measured during exercise or work of the human body, the sensors and the wires hinder a movement of the human body.

In addition, when the sensors and the wires are mounted on the human body (particularly in a case where the sensors the wires are mounted on the plurality of locations), it is desirable that the sensors and the wires need to be thin and light and can be easily mounted on the human body. In addition, low cost is also an important factor.

Therefore, an object of the present invention is to provide a biological data measurement device which is easily mounted on a human body with a simple and inexpensive configuration, and which has patches (sensor units) that do not increase the number of wires even in a case where the patches are mounted on a plurality of locations of the human body.

Solution to Problem

According to the present invention, in order to solve the above-described problems, there is provided a biological data measurement device including a patch including a first heat insulator disposed on a body surface of a living body which is a measurement object, a second heat insulator layered on the first heat insulator, a belt-shaped conductor film that is wired over at least a layered surface between the first heat insulator and the second heat insulator from a bottom surface of the first heat insulator on the body surface side, a first temperature measurement circuit including a first thermometer, and disposed on the conductor film on the bottom surface side of the first heat insulator, and a second temperature measurement circuit including a second thermometer, and disposed on the conductor film in the layered surface.

It is preferable that both surfaces of the conductor film are covered with an electrically insulating film except for an electrical connection portion connected to each of the temperature measurement circuits.

In addition, preferably, a biocompatible skin contact layer including a wiring portion of the conductor film is disposed on the bottom surface of the first heat insulator on the body surface side.

As one aspect of the present invention, the first temperature measurement circuit and the second temperature measurement circuit may be connected in series to a bus wire included in the conductor film, and each of the temperature measurement circuits may be equipped with a selection circuit that turns on and off an output of a temperature signal measured by the thermometer. The term referred to as series in the present specification represents a case where the circuits are viewed in a block diagram. As can be understood when viewing the circuits inside the block diagram, the analog line, the power supply line, and the ground line directly output an input. Therefore, in a case where the block is internally viewed, some portions are connected in parallel.

The selection circuit has a function of selectively outputting the temperature signal measured by the first thermometer and the temperature signal measured by the second thermometer at a predetermined timing.

As a preferred aspect, the selection circuit includes a latch circuit that is operated by a selection signal from an outside, and a semiconductor switch that is turned on and off by an output of the latch circuit, the bus wire includes an analog line for reading the temperature signal, a power supply line, and a ground line, and the thermometer is connected between the analog line and the ground line via the semiconductor switch.

In addition, according to an aspect of the present invention, the biological data measurement device may include a plurality of the patches. The respective patches are connected in series via the conductor film including the bus wire.

In addition, corresponding to a DHF method, the present invention also includes an aspect in which the number of the patches is an even number, and in which thicknesses of the heat insulators are different from each other between an odd-numbered first patch and an even-numbered second patch.

According to a preferred aspect of the present invention, a plurality of the patches are supported by a mounting belt for a human body in a state where the patches are connected in series via the conductor film including the bus wire.

In addition, a plurality of patches may be disposed on a garment in a state where the patches are connected in series via the conductor film including the bus wire.

According to a preferred aspect of the present invention, the conductor film has contact portion including a first connection terminal connected to the analog line, a second connection terminal connected to the power supply line, and a third connection terminal connected to the ground line.

The contact portion may be disposed in the conductor film existing between the patches, or may be disposed on an upper surface of the second heat insulator of the patch.

The biological data measurement device according to the present invention may further include a signal processor that can be electrically and mechanically attached to and detached from the contact portion, that provides the latch circuit with a control clock for a power supply and a latch operation, and that performs predetermined processing on a temperature signal by collecting the temperature signal from each of the thermometers.

The signal processor may include an arithmetic unit that obtains a heat flow Ith from $(Tsk-Tsub)/Rthins$, when a body surface temperature measured by the first thermometer is denoted by $Tsk$, a temperature of the layered surface measured by the second thermometer is denoted by $Tsub$, heat resistance of the first heat insulating layer is denoted by $Rthins$, and a heat flow that flows substantially perpendicular to the body surface is denoted by $Ith$.

In addition, the present invention may include an aspect as follows. The number of the patches is an even number, and thicknesses of the heat insulators are different from each other between an odd-numbered first patch and an even-numbered second patch. When a body surface temperature measured by the first thermometer of the first patch is denoted by $Tsk1$, a heat flow that flows substantially perpendicular to the body surface in a temperature measurement portion thereof is denoted by $Ith1$, a body surface temperature measured by the first thermometer of the second patch is denoted by $Tsk2$, a heat flow that flows substantially perpendicular to the body surface in a temperature measurement portion thereof is denoted by $Ith2$, and internal heat resistance from a core tissue of the living body to the body surface is denoted by $Rthbody$, the arithmetic unit calculates $Rthbody$ from $(Tsk2-Tsk1)/(Ith1-Ith2)$, and thereafter, obtains a core body temperature $Tcore$ of the living body from $(Ith1 \times Rthbody+Tsk1)$ or $(Ith2 \times Rthbody+Tsk2)$.

Advantageous Effects of Invention

According to the present invention, the patch (sensor unit) is basically configured to include the two first and second heat insulators, the two first and second temperature measurement circuits, and the belt-shaped conductor film. Therefore, the configuration is simple. For example, a thickness can be approximately several mm, and a weight can be approximately several grams. The patch is easily mounted on the human body, and is inexpensive. The patch is equipped with the selection circuit, and selectively outputs the temperature signal of the first thermometer and the temperature signal of the second thermometer at a predetermined timing. Accordingly, even in a case where the patches are mounted on a plurality of locations of the human body, the number of wires is settled by the number required for one patch. The number of wires can be significantly reduced, compared to the number of wires in the related art.

BRIEF DESCRIPTION OF DRAWINGS

FIG. 8(a) is a schematic perspective view illustrating a mounting belt for mounting a plurality of patches on a human body, FIG. 8(b) is a schematic perspective view illustrating the plurality of patches connected in series to the mounting belt, and FIG. 8(c) is a schematic perspective view illustrating a state where the plurality of patches are mounted on the mounting belt.

FIG. 11(a) is a schematic sectional view of a patch in which a contact portion is disposed on an upper surface of the patch, and FIG. 11(b) is a plan view thereof.

FIG. 12(e) is a schematic sectional view illustrating a fifth example of the electrical/mechanical contact portion.

FIG. 13(a) is a schematic view illustrating an example in which a portion of a conductor film of the patch is used as an electrode for detecting an electrocardiographic signal, and FIG. 13(b) is an enlarged sectional view of the electrode portion.

DESCRIPTION OF EMBODIMENTS

Figure 1A:
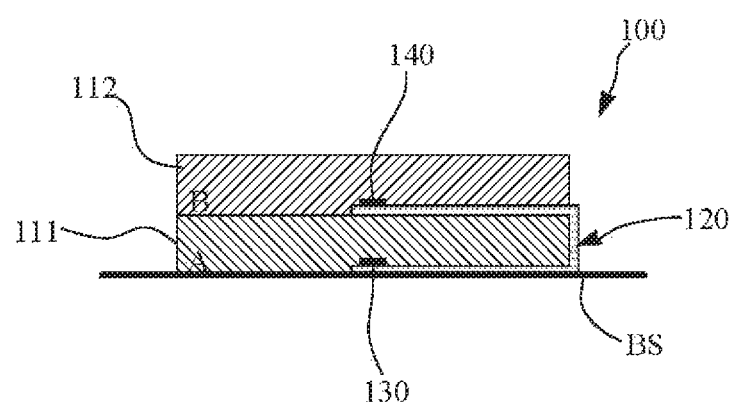
FIG. 1(a) is a schematic sectional view illustrating a basic aspect (first embodiment) of a patch included in a biological data measurement device according to the present invention.
Figure 1B:
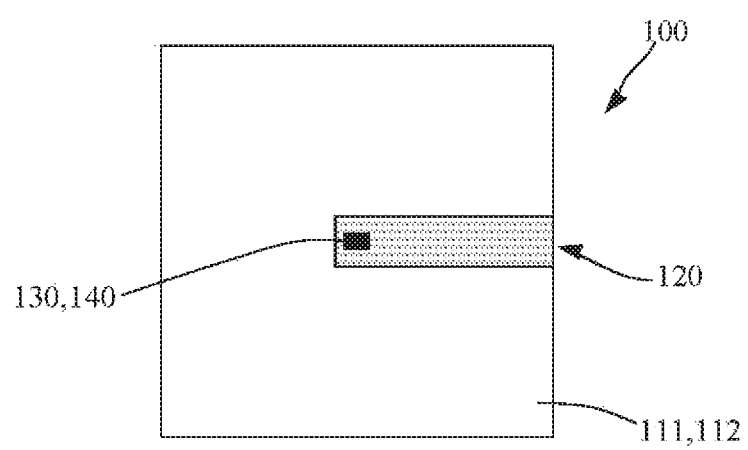
FIG. 1(b) is a schematic plan view including a temperature measurement circuit.

Next, some embodiments according to the present invention will be described with reference to 1(a) to 18. However, the present invention is not limited to the embodiments.

First, referring to FIGS. 1(a) to 3, as a first embodiment of a basic configuration, a biological data measurement device according to the present invention includes a patch 100 used as a sensor unit to be mounted on a body surface of a living body.

The patch 100 includes two first and second heat insulators 111 and 112, a belt-shaped wiring film (also referred to as a bus wire) 120, and two first and second two temperature measurement circuits 130 and 140.

When the first heat insulator 111 is disposed on a body surface BS, the second heat insulator 112 is stacked on the first heat insulator 111. As the heat insulators 111 and 112, a foam material, particularly foamed plastic such as foamed polystyrene and foamed polyurethane is preferably used.

Thermal conductivity of the foamed plastic varies depending on an expansion ratio. However, when the thermal conductivity is 0.1 W/m/K or lower, and preferably 0.05 W/m/K or lower, heat insulating capability or strength is satisfactory. A thickness of the respective heat insulators 111 and 112 is 3 mm or shorter, and preferably 1 mm or shorter from a viewpoint of easy mounting. However, in order to obtain a sufficient S/N ratio, it is necessary to improve the heat insulating capability by increasing the thickness.

It is preferable that a contact layer made of a biocompatible material is formed on a surface of the first heat insulator 111 which comes into contact with a body surface (skin). A material having a silicon component can be used as the biocompatible material of the contact layer.

For the purpose of waterproofing, the whole patch can be wrapped with a biocompatible material to prevent sweat or moisture from entering the heat insulators 111 and 112, the wiring film 120, and the temperature measurement circuits 130 and 140. In addition, the heat insulators 111 and 112 can be filled with an adhesive for waterproofing.

The wiring film 120 has a belt-shaped (ribbon-shaped) conductor film 121 serving as a core wire. In the present embodiment, both surfaces of the conductor film 121 are covered with insulating films 122 and 122. As the insulating film 122, it is preferable to use a polymer film that has satisfactory biocompatibility and is less likely to cause a problem such as rash. For example, siloxane or silicon rubber (silicone) may be used.

The conductor film 121 is formed of a metal material, and preferably copper, silver, or gold. As an example, the conductor film 121 is formed in a belt shape on one insulating film 122, and the other insulating film 122 is covered from above. In this manner the wiring film 120 is formed. However, it is preferable that the thickness of the whole wiring film 120 is several tens to several hundreds of microns.

The wiring film 120 is wired from at least a bottom surface A of the first heat insulator 111 which comes into contact with the body surface BS to a layered surface B between the first heat insulator 111 and the second heat insulator 112 via a side surface of the first heat insulator 111. The whole bottom surface A of the first heat insulator 111 may be covered with the insulating film 122.

The first temperature measurement circuit 130 includes a thermometer 131 and a selection circuit 132 that permits an access to the thermometer 131. Similarly, the second temperature measurement circuit 140 also includes a thermometer 141 and a selection circuit 142 that permits an access to the thermometer 141.

As the thermometers 131 and 141, a thermistor, a thermocouple, a semiconductor such as a diode, or a radiation thermometer may be used. The selection circuits 132 and 142 connect the thermometers 131 and 141 to analog lines in a bus wire (to be described later) at a predetermined timing.

The first temperature measurement circuit 130 is disposed on the wiring film 120 on the bottom surface A of the first heat insulator 111, and the second temperature measurement circuit 140 is disposed on the wiring film 120 on the layered surface B between the first heat insulator 111 and the second heat insulator 112.

Figure 2A:
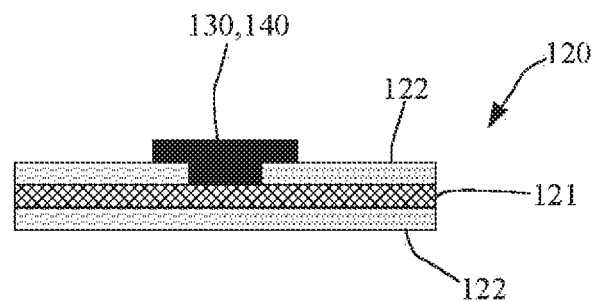
FIG. 2(a) is a schematic sectional view illustrating a first connection aspect to a conductor film of the temperature measurement circuit.
Figure 2B:
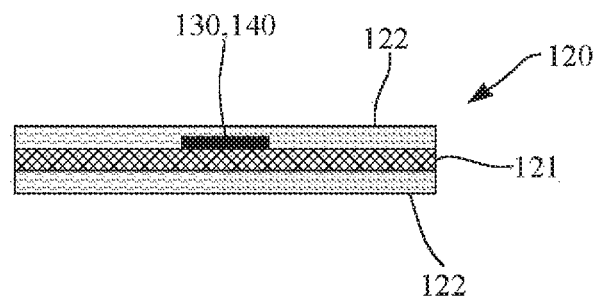
FIG. 2(b) is a schematic sectional view illustrating a second connection aspect.
Figure 3:
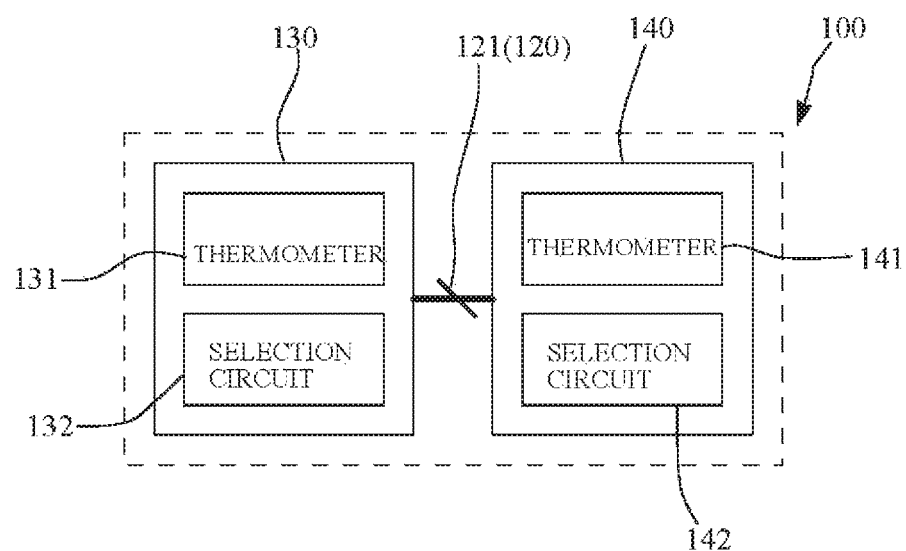
FIG. 3 is a block diagram schematically illustrating an electrical configuration of the patch according to the first embodiment.

As illustrated in FIG. 2(a), the temperature measurement circuits 130 and 140 can be electrically connected to the conductor film 121 by forming an opening portion in a portion of the insulating film 122 on an upper surface side so that the conductor film 121 is exposed. However, as illustrated in FIG. 2(b), the insulating film 122 may be disposed between the insulating film 122 and the conductor film 121 without forming the opening portion in the portion of the insulating film 122. According to an aspect illustrated in FIG. 2(b), in a case where the temperature measurement circuits 130 and 140 are made of semiconductor chips, the semiconductor chips can be effectively protected.

When a body surface temperature measured by the first thermometer 131 is denoted by Tsk, a temperature of the layered surface B measured by the second thermometer 141 is denoted by Tsub, heat resistance of a first heat insulating layer 11 is denoted by Rthins, and a heat flow that flows substantially perpendicular to the body surface BS is denoted by Ith, the heat flow Ith is obtained from (Tsk−Tsub)/Rthins.

Here, when a core body temperature of the living body is denoted by Tcore, and the heat resistance from a core tissue of the living body to the body surface BS is denoted by internal heat resistance Rthbody, the core body temperature Tcore can be obtained from Tcore=Tsk+Ith×Rthbody.

In the first embodiment, the internal heat resistance Rthbody is measured using another method (not illustrated). As an example of the method, the following method is known. A weak current (for example, about 0.2 ρA) is caused to flow into the living body from a pair of electrodes. The internal heat resistance Rthbody is estimated, based on an internal electrical resistance value measured by internal electrical resistance measurement means for measuring electrical resistance (GSR: Galvanic Skin Resistance) inside the living body.

Figure 4:
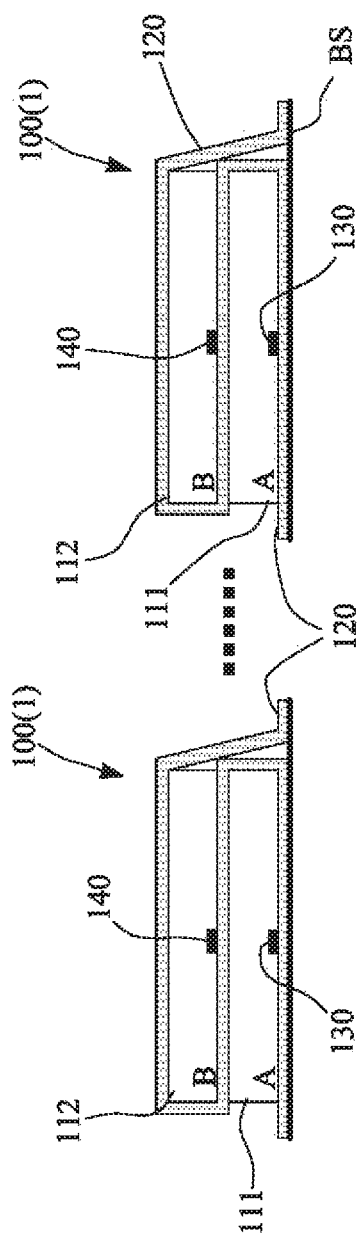
FIG. 4 is a schematic sectional view illustrating an aspect in which a plurality of the patches are connected in series as a second embodiment according to the present invention.

Next, a second embodiment according to the present invention will be described with reference to FIG. 4. In the second embodiment, a plurality of the patches 100 (100(1) to 100(n)) are connected in series (single stroke drawing form) via the wiring film 120.

That is, in the second embodiment, the wiring film 120 is laid around in the order of the bottom surface A of the first heat insulator 111 of the first patch 100(1)→a side surface of the first heat insulator 111 (right side surface in FIG. 4)→the layered surface B between the first heat insulator 111 and the second heat insulator 112→a side surface of the second heat insulator 112 (left side surface in FIG. 4)→an upper surface of the second heat insulator 112. Thereafter, the wiring film 120 is wired along a side surface of the patch 100(1) (right surface in FIG. 4) to reach the bottom surface A of the first heat insulator 111 of the second patch 100(2). In this manner, the wiring is repeatedly performed.

Figure 5:
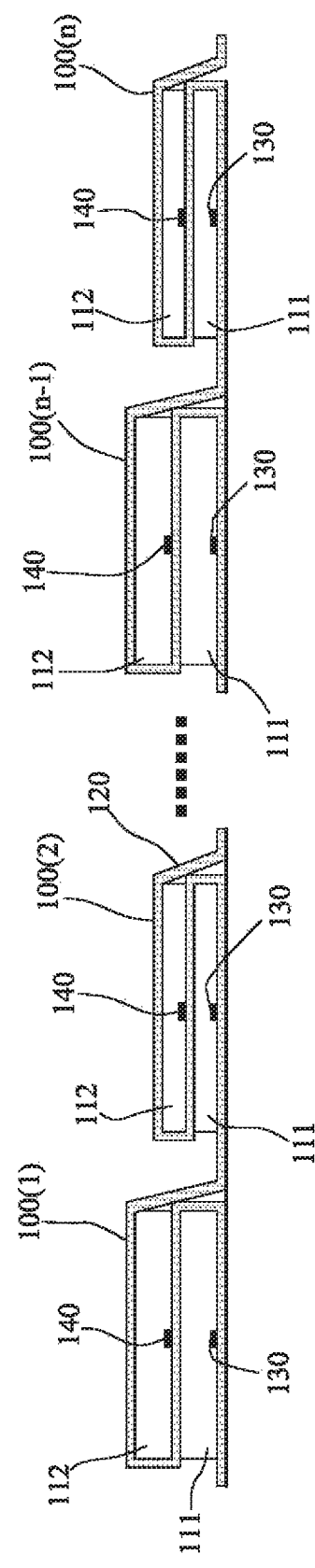
FIG. 5 is a schematic sectional view illustrating another example of the second embodiment.

As another example of the second embodiment, as illustrated in FIG. 5, out of n number (even number) of patches 100(1) to 100(n), for example, the thickness of the heat insulators 111 and 112 of the even-numbered patches 100(2), 100(4), 100(6), and so forth is thinned than the thickness of the heat insulators 111 and 112 of the odd-numbered patches 100(1), 100(3), 100(5), and so forth. In this manner, the heat resistance Rthbody can be calculated to obtain the core body temperature Tcore by using the DHF method. In this case, the odd-numbered patch and the even-numbered patch which are adjacent to each other are used as a pair.

The first patch 100(1) and the second patch 100(2) will be described as an example. When a body surface temperature measured by the first thermometer 131 of the first patch 100(1) is denoted by Tsk1, a heat flow that flows substantially perpendicularly to the body surface in a temperature measurement portion thereof is denoted by Ith1, a body surface temperature measured by the first thermometer 131 of the second patch 100(2) is denoted by Tsk2, a heat flow that flows substantially perpendicular to the body surface in a temperature measurement portion thereof is denoted by Ith2, and internal heat resistance from the core tissue of the living body to the body surface is denoted by Rthbody, the internal heat resistance Rthbody is calculated from (Tsk2−Tsk1)/(Ith1−Ith2). In this manner, a core body temperature Tcore is calculated from (Ith1×Rthbody+Tsk1) or (Ith2×Rthbody+Tsk2).

In this way, according to the embodiment adopting the DHF method in FIG. 5, an absolute value of the core body temperature at the n-number of locations can be obtained using the 2n-number of patches in total.

As illustrated by the block diagram in FIG. 5, in the second embodiment, the respective patches 100 are connected in series via the conductor film 121 inside the wiring film 120. However, according to the present invention, due to the presence of the selection circuits 132 and 142, the number of wires does not increase even if the number of connected patches increases.

Figure 6:
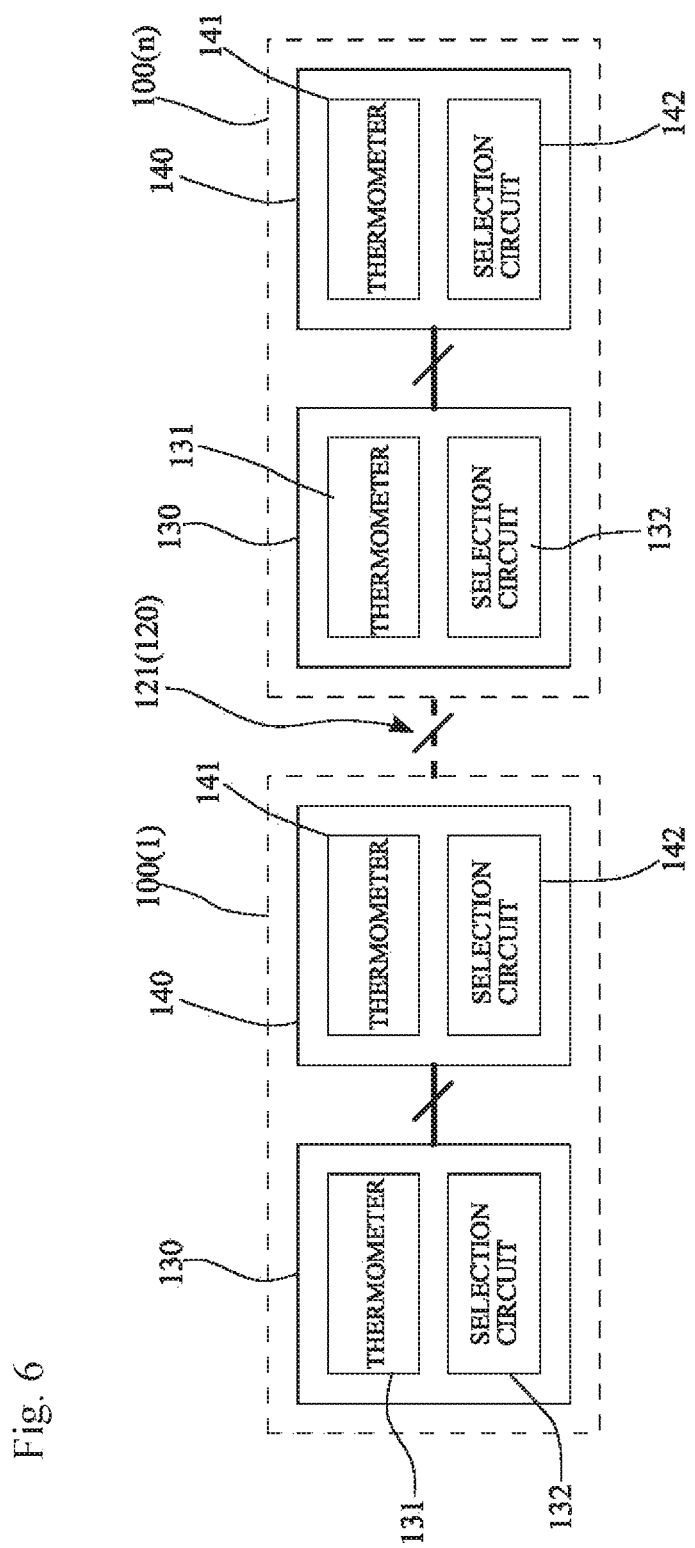
FIG. 6 is a block diagram schematically illustrating an electrical configuration of the second embodiment.
Figure 7:
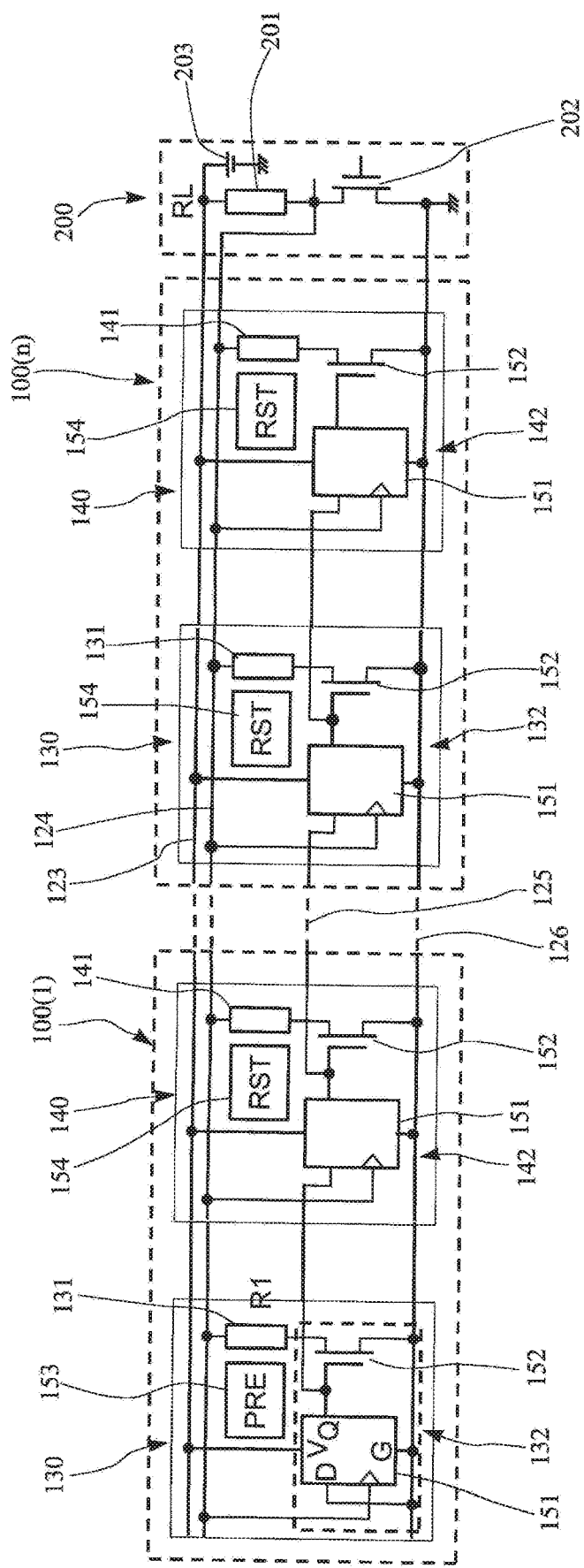
FIG. 7 is a circuit diagram illustrating a specific configuration example of the block diagram in FIG. 6.

Referring to the block diagram in FIG. 6 and the circuit diagram in FIG. 7, in addition to the selection circuit 132 of the first temperature measurement circuit 130 and the selection circuit 142 of the second temperature measurement circuit 140, the patch 100 includes a latch circuit 151 and a semiconductor switch 152 that is turned on and off by an output of the latch circuit 151. In this example, a MOSFET is used as the semiconductor switch 152. Accordingly, herein, the semiconductor switch will be referred to as the MOSFET. In addition, a flip-flop circuit is used as the latch circuit 151.

The conductor film 121 internally includes a power supply line 123, an analog line 124 that also serves as a clock line, a data line 125, and a ground (GND) line 126. One end of the thermometers (for example, thermistors) 131 and 141 is connected to the analog line 124, and the other end is connected to a drain of the MOSFET 152.

A gate of the MOSFET 152 is connected to an output terminal Q of the latch circuit 151. For example, an N type is used as the MOSFET. A power supply terminal V of the latch circuit 151 is connected to the power supply line 123, and a ground terminal G is connected to the ground line 126.

A preset circuit 153 that presets the latch circuit 151 when the power is turned on is disposed only in the first temperature measurement circuit 130 of the leading (first) patch 100(1). For example, the preset circuit 153 has a resistance element and a capacitor, and delays a rise of the power supply.

The latch circuit 151 other than the leading latch circuit has a reset circuit 154, and resets the latch circuit 151 when the power is turned on. A data input terminal D of the leading latch circuit 151 is connected to the ground line 126 so that "0" is input when a clock is input. An output terminal Q of the latch circuit 151 is connected to the data input terminal D of the subsequent latch circuit 151. The analog line 124 which also serves as a clock line is connected to a clock terminal of the latch circuit 151.

The power supply line 123, the analog line 124, and the ground line 126 are connected to a signal processor 200 via a contact portion (to be described later with reference to FIGS. 10 and 11). The signal processor 200 includes a load resistor 201, a semiconductor switch (MOSFET) 202, and a battery 203 as a built-in power source.

One end of the load resistor 201 is connected to the battery 203, and the other end is connected to a connection point between the analog line 124 and a drain of the MOSFET 202. A source of the MOSFET 202 is connected to the ground line 126, and a clock signal is input to a gate of the MOSFET 202.

In this manner, when the power is turned on, a state of the respective latch circuits 151 is "100 . . . ". The thermometer (thermistor) 131 inside the first temperature measurement circuit 130 of the leading patch 100(1) is selected. When a resistance value thereof is denoted by R1, and a resistance value of the load resistor 201 is denoted by RL, a voltage (=V×R1/(RL+R1)) obtained by dividing a power supply voltage V into RL and R1 appears in the analog line 124.

The subsequent clock input to the gate of the MOSFET 202 is used. In this case, the thermometer (thermistor) 141 inside the second temperature measurement circuit 140 of the leading patch 100(1) is selected. When a resistance value thereof is denoted by R2, a voltage of V×R2/(RL+R2) appears in the analog line 124. In this way, the thermometers 131 and 141 are sequentially and alternately shifted each time the clock is input to the gate of the MOSFET 202.

According to this configuration, the required number of wires (wires made of the conductor film) inside the wiring film 120 is only four. In addition, the signal processor 200 needs only three contacts. The number of wires and the number of contacts are not changed even if the number of patches increases.

For example, each of the thermometers 131 and 141 may read the temperature once in one second. Even in a case where the core body temperature Tcore is suddenly changed due to running, the change is approximately 0.2° C. in one minute, and a change amount thereof is 0.01° C. or lower in one second. Accordingly, even if the temperature is read every second, there is no problem.

In a case where 10 patches is read as n and 20 thermometers are read, if the respective thermometers are read at a frequency of approximately 20 Hz, all of the thermometers can be read in one second.

Figure 8A:
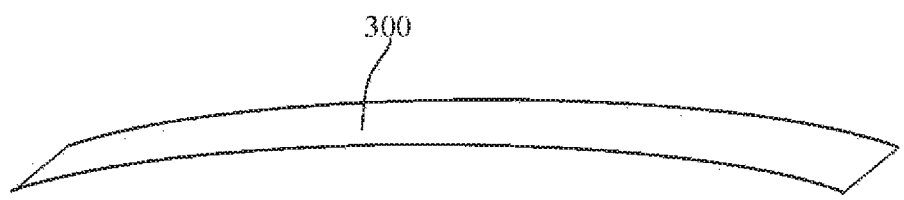
FIGS. 8(a), 8(b) and 8(c) illustrate third embodiments according to the present invention.
Figure 8B:
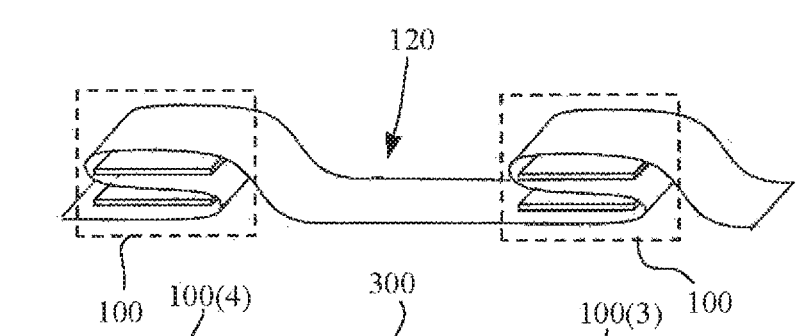
Figure 8C:
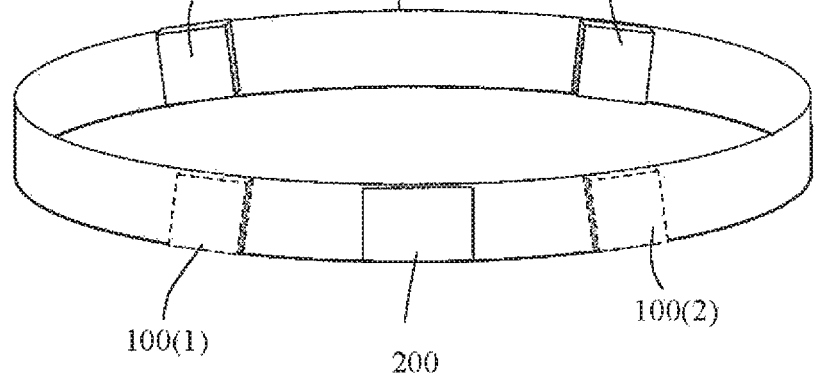

FIGS. 8(a), 8(b) and 8(c) illustrate a first example of mounting the patch on the human body as a third embodiment. In the mounting example, a long belt 300 as illustrated in FIG. 8(a) is used. It is preferable that a material of the belt 300 is a rubber-like and a biocompatible material that is highly stretchable to be in close contact with the skin.

As illustrated in FIG. 8(b), a patch row in which a plurality of the patches 100 are electrically and mechanically connected via the wiring film 120 is attached to the belt 300. As illustrated in FIG. 8(c), for example, four patches 100(1) to 100(4) are attached to the belt 300. In this manner, right and left sides of an abdomen or a back can be measured.

In this case, the signal processor 200 is disposed at any desired position in the belt 300, and is connected to the conductor film 121 inside the wiring film 120 via a contact portion (to be described later) to sequentially collect temperature measurement signals (voltage signals appearing on the analog line 124) of the respective thermometers (8 thermometers).

Figure 9:
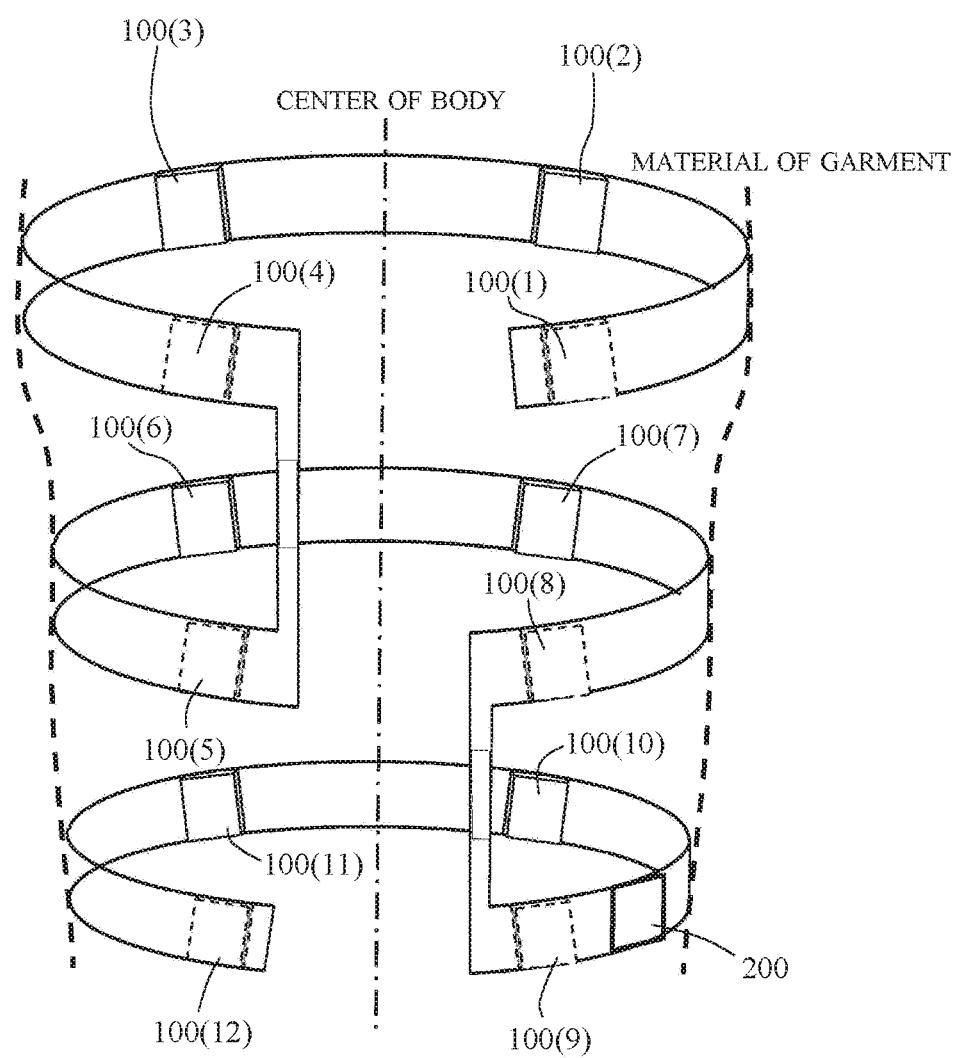
FIG. 9 is a schematic view illustrating an aspect in which a plurality of patches are disposed on a garment worn on a human body as a fourth embodiment according to the present invention.

FIG. 9 illustrates a second example of mounting the patch on the human body as a fourth embodiment. In the mounting example, similarly to the above-described example, the patch row in which a plurality of the patches 100 are electrically and mechanically connected via the wiring film 120 is used by being attached to a material of a garment.

For example, twelve patches 100(1) to 100(12) as n are disposed on the material of the garment. In this manner, upper, middle, lower, right, and left sides of the abdomen or the back can be measured. Even in this case, for example, the signal processor 200 is disposed at a waist position, and is connected to the conductor film 121 inside the wiring film 120 via a contact portion (to be described later) to sequentially collect temperature measurement signals (voltage signals appearing on the analog line 124) of the respective thermometers (24 thermometers).

In this way, the body temperatures are measured at a plurality of locations. Accordingly, for example, a temperature around a rectum (usually, the temperature is not changed much from 37° C.) is compared with a temperature around a stomach (the temperature is likely to be changed due to autonomic nerves or environmental temperatures). Based on a comparison result, It is possible to recognize how temperature control is performed on autonomic nerves of a person having the mounted patch.

The patch 100 may be formed to be in contact with the body surface (skin surface). In addition, a belt or a clothing material can be regarded as a portion of the skin, and the skin to the belt or the clothing material to the patch can be formed in this order.

Next, referring to FIG. 10, a configuration of an electrical connection portion (contact portion) between the patch 100 and the signal processor 200 will be described as a fifth embodiment.

Out of the power supply line 123, the analog line 124, the data line 125, and the ground (GND) line 126 which are included in the conductor film 121, three lines 123, 124, and 126 other than the data line 125 need to be electrically connected to the signal processor 200.

Figure 10:
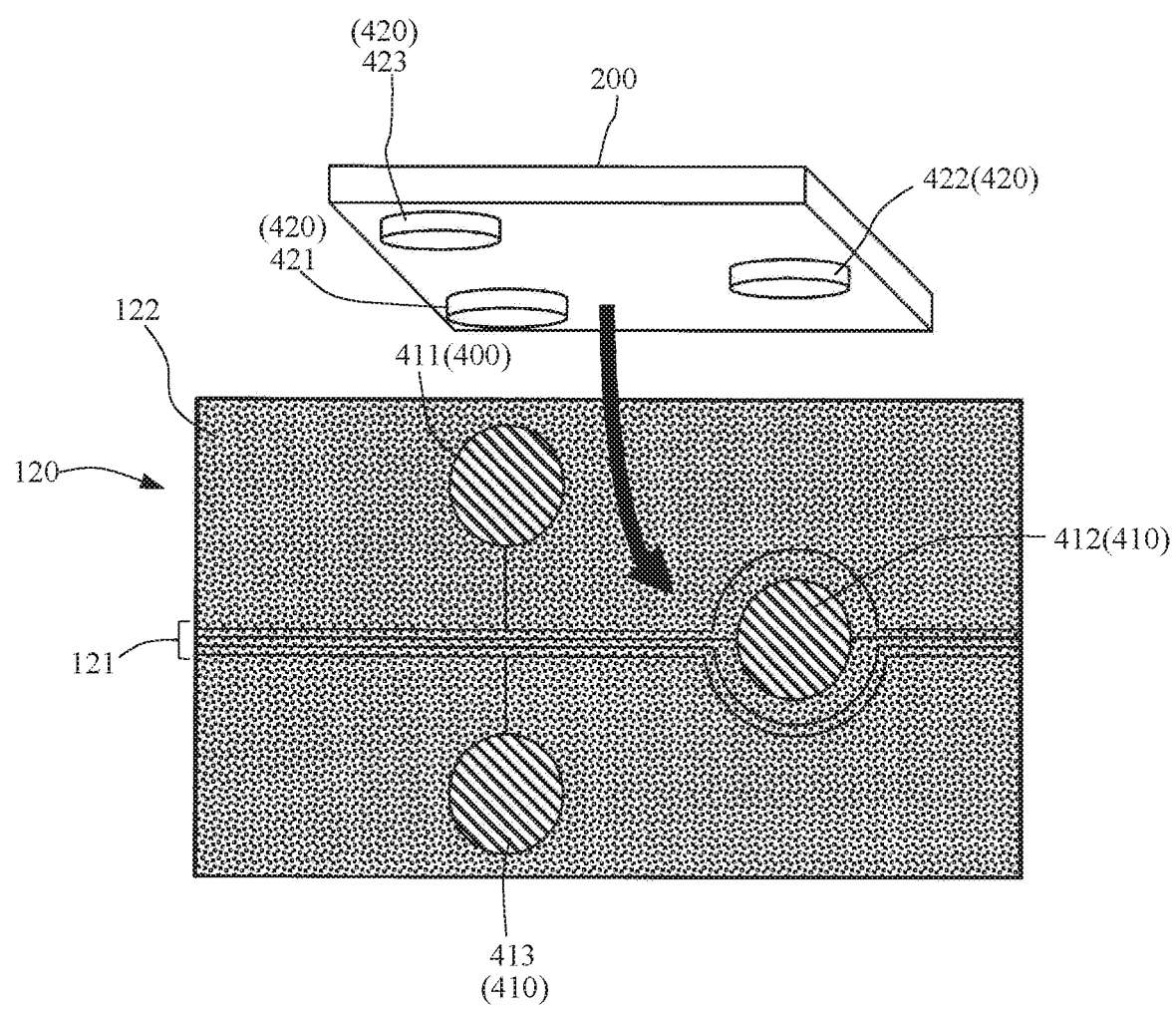
FIG. 10 is a schematic view illustrating a connection aspect between a patch and a signal processor as a fifth embodiment according to the present invention.

FIG. 10 illustrates an example in which the contact portion is disposed at a predetermined location of the wiring film 120, and three connection terminals 410 are disposed on the wiring film 120 side. That is, the connection terminal 410 on the wiring film side includes a first connection terminal 411 connected to the power supply line 123, a second connection terminal 412 connected to the analog line 124, and a third connection terminal 413 connected to the ground line 126. In a case where it is not necessary to distinguish the connection terminals 411, 412, and 413 from each other, all of these will be collectively referred to as the connection terminal 410.

In contrast, three connection terminals 420 are also disposed on the signal processor 200 side. That is, the connection terminal 420 on the signal processor side includes a first connection terminal 421 corresponding to the first connection terminal 411 on the wiring film side, a second connection terminal 422 corresponding to the second connection terminal 412 on the wiring film side, and a third connection terminal 423 corresponding to the third connection terminal 413 on the wiring film side. In a case where it is not necessary to distinguish the connection terminals 421, 422, and 423 from each other, all of these will be collectively referred to as the connection terminal 420.

It is preferable that the connection terminal 410 on the wiring film side is made of a conductive magnetic material. As the connection terminal 410 on the wiring film side, an iron material plated with gold, silver, or nickel can be used. In addition, the connection terminal 410 on the wiring film side can be formed of a solder material or a conductive adhesive. A caulking metal fitting (to be described later) may be used.

Similarly, it is preferable to use the conductive magnetic material for the connection terminal 420 on the facing signal processor side. The signal processor 200 may be put into a plastic case, or may be molded and sealed as a semiconductor chip.

Any one or both of the connection terminal 410 on the wiring film side and the connection terminal 420 on the signal processor side which are made of the conductive magnetic material may be magnetized (polarized). In this manner, self-aligned contact may be available as the signal processor 200 is moved closer.

Figure 11A:
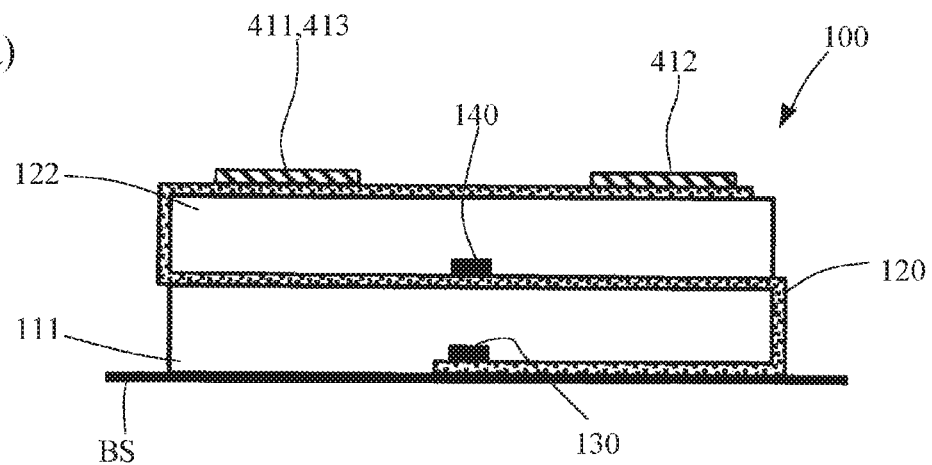
FIGS. 11(a) and 11(b) another example of the fifth embodiment.
Figure 11B:
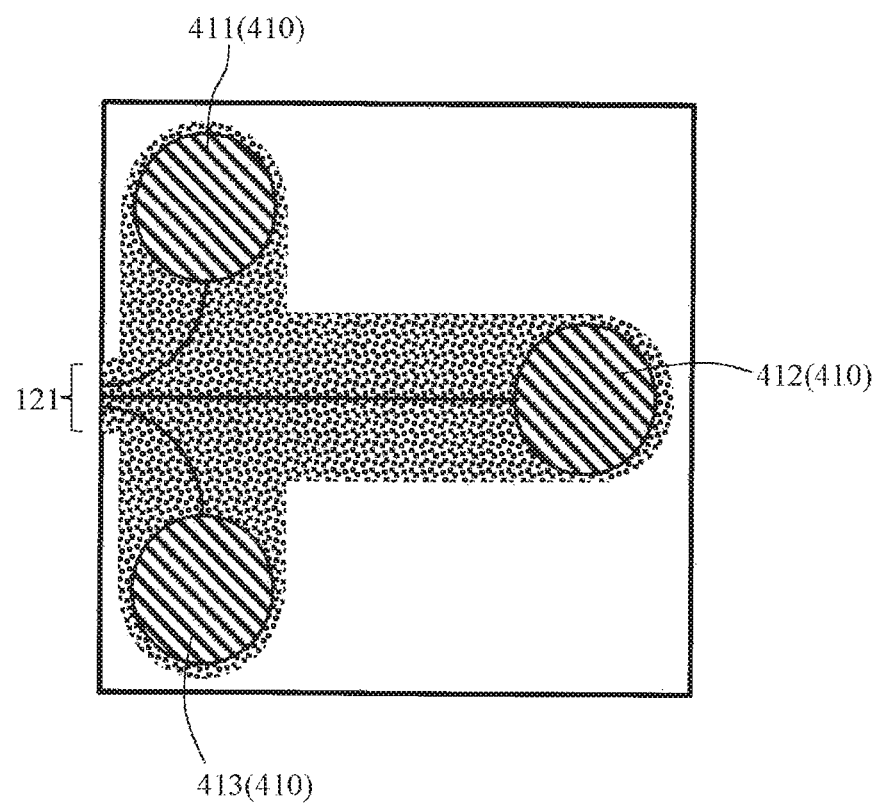

As another example of the contact portion in the fifth embodiment, as illustrated in FIGS. 11(a) and 11(b), the connection terminals 410 (411, 412, and 413) on the wiring film side can also be installed directly above the second heat insulator 112 of the patch 100. This example has an advantage in that the configuration is compact. Particularly, this example is suitable to a case where the temperature is measured at one location.

Next, referring to FIGS. 12(a) to 12(e), as a sixth embodiment, some configuration examples of electrical/mechanical contact portions between the connection terminal 410 on the wiring film side and the connection terminal 420 on the signal processor side will be described.

Figure 12A:
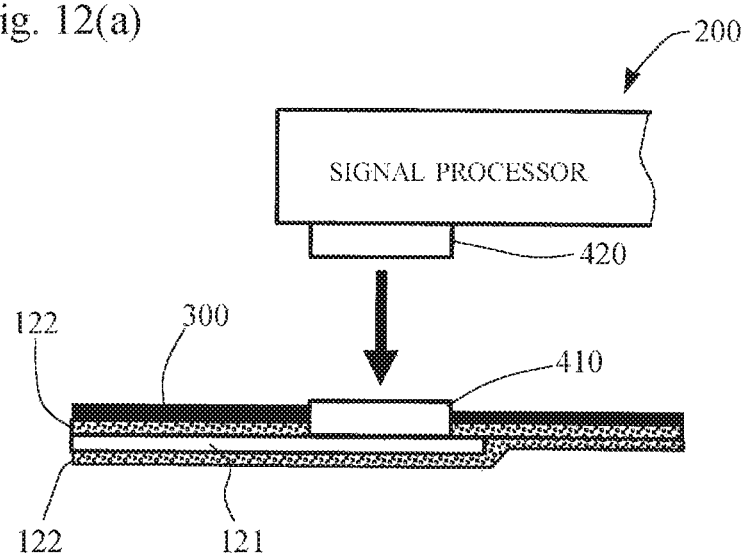
FIG. 12(a) is a schematic sectional view illustrating a first example of an electrical/mechanical contact portion between a patch and a signal processor in a sixth embodiment according to the present invention.

First, in the first example of FIG. 12(a), both the connection terminal 410 on the wiring film side and the connection terminal 420 on the signal processor side are made of conductive magnets. The conductive magnet is generally a coin-shaped or button-shaped disc. However, a rectangular shape may be used. In a case of magnets, there is an advantage in that center positions of the magnets are automatically aligned (coincident) with each other. The conductive magnet and the conductor film 121 are electrically and mechanically connected using a conductive adhesive.

Figure 12B:
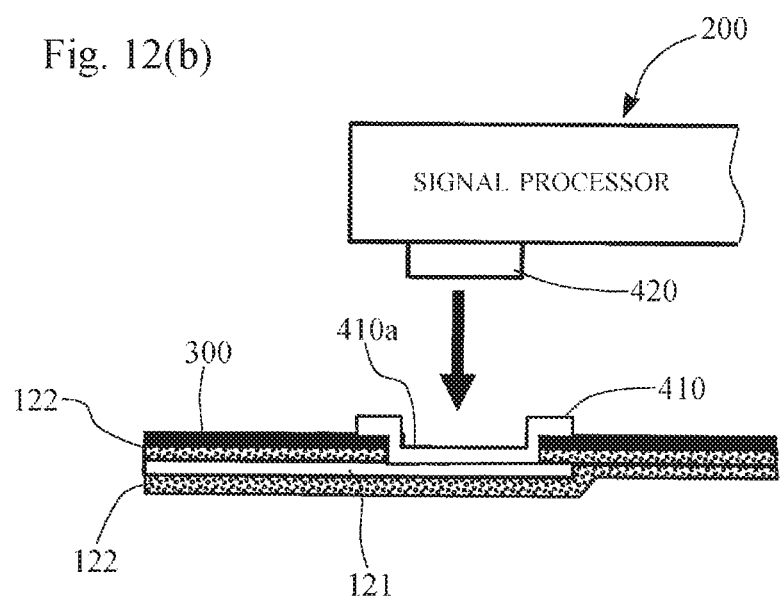
FIG. 12(b) is a schematic sectional view illustrating a second example of the electrical/mechanical contact portion.

Next, in the second example of FIG. 12(b), the connection terminal 420 on the signal processor side is the conductive magnet. However, the connection terminal 410 on the wiring film side is a conductive magnetic material such as iron. In this case, the connection terminal 410 on the wiring film side may have a recess portion 410a into which the connection terminal 420 on the signal processor side is fitted.

As in the first example, a conductive adhesive may be used to electrically and mechanically connect the conductive magnetic material and the conductor film 121 to each other. As another aspect, the conductive magnetic material of the connection terminal 410 on the wiring film side may be plated with Ag. Heat sealing of Ag to Ag may be performed between the conductor film 121 and the conductive magnetic material.

Figure 12C:
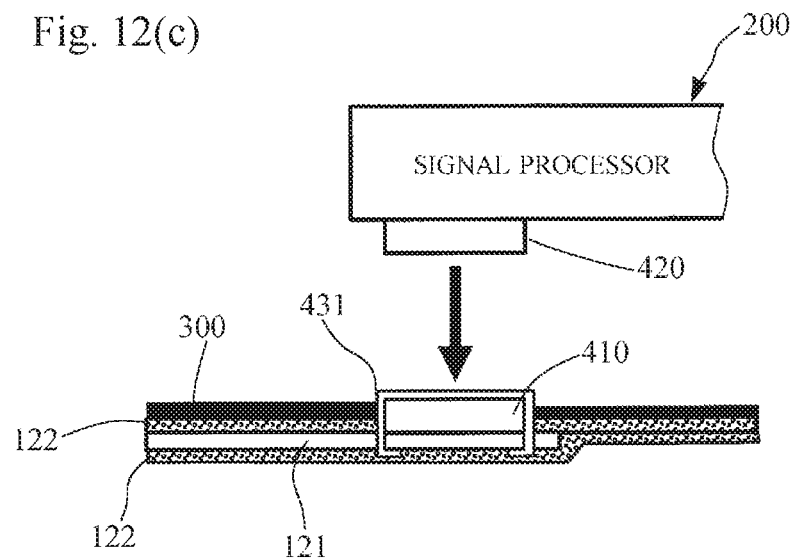
FIG. 12(c) is a schematic sectional view illustrating a third example of the electrical/mechanical contact portion.

The third example of FIG. 12(c) is a modification example of the first example. The conductive magnet used as the connection terminal 410 on the wiring film side is fixed to the conductor film 121 by using a gate-shaped caulking needle 431. After the caulking, the caulked portion is covered with the insulating film 122.

Figure 12D:
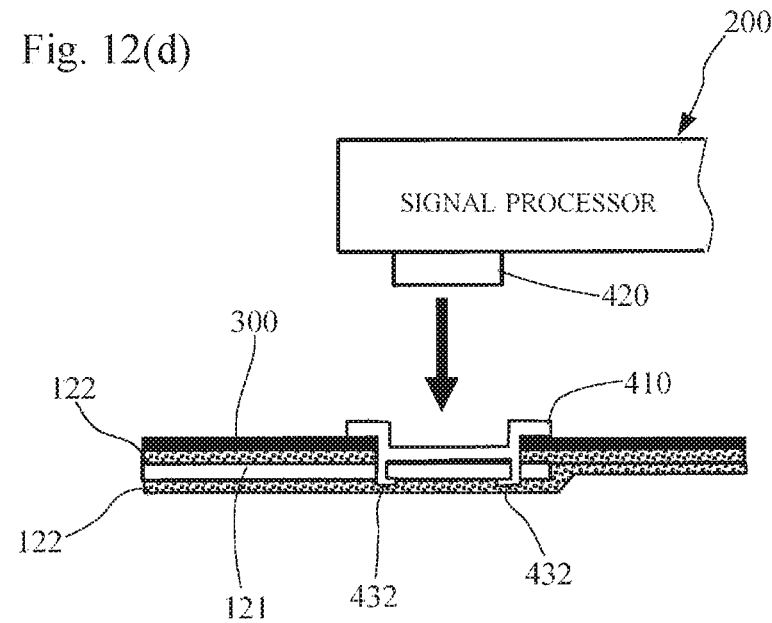
FIG. 12(d) is a schematic sectional view illustrating a fourth example of the electrical/mechanical contact portion.

The fourth example of FIG. 12(d) is a modification example of the second example. A caulking leg 432 is formed on the conductive magnetic material itself used as the connection terminal 410 on the wiring film side. The caulking leg 432 is cut into and fixed to the conductor film 121. Even in this case, the insulating film 122 is covered after the caulking.

In the fifth example of FIG. 12(e), for example, the connection terminal 410 on the wiring film side which is made of the conductive magnet is disposed on the belt 300, and is temporarily fixed by using a caulking receiving ring 433. Thereafter, a cup-shaped caulking metal fitting 434 is put into the caulking receiving ring 433 from a rear surface side of the conductor film 122. In this manner, The connection terminal 410 on the wiring film side is permanently fixed. A bottom portion of the caulking metal fitting 434 is covered with the insulating film 122. In the fifth example, the connection terminal 410 on the wiring film side is electrically connected to the conductor film 121 via the caulking metal fitting 434.

Figure 13A:
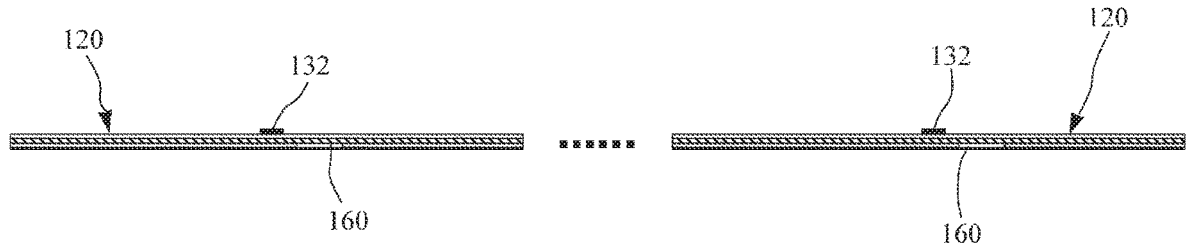
FIGS. 13(a) and 13(b) illustrate seventh embodiments.

Next, referring to FIGS. 13 to 15, as a seventh embodiment, a configuration will be described in which a biological signal is read from a plurality of electrodes by using the wiring film 120 without increasing the number of wires.

The biological signal read through the electrodes includes various signals such as Electrocardiogram (ECG), Galvanic Skin Resistance (GSR: skin (internal) electrical resistance), Electrical Impedance Tomography (EIT: electrical impedance), Electromyography (EMG: myoelectricity), and Electroencephalogram (EEG: electroencephalograph).

Figure 13B:
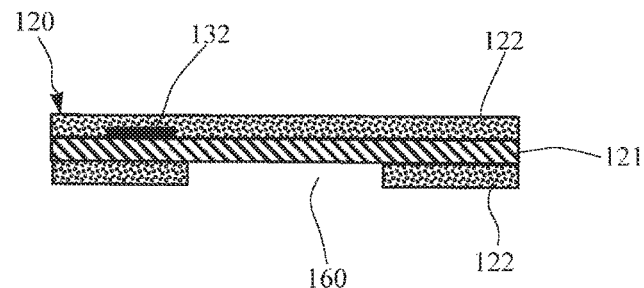
Figure 14:
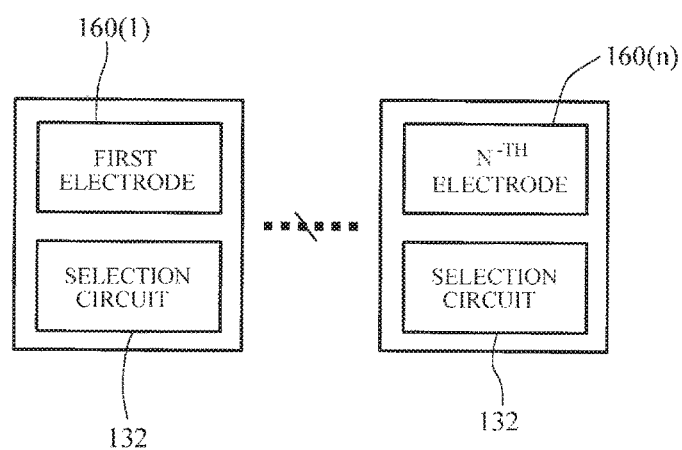
FIG. 14 is a block diagram schematically illustrating an electrical configuration of the seventh embodiment.

As illustrated in FIG. 13(b), an electrode 160 can be formed as follows. An opening portion is disposed in a portion of the insulating film 122 on one side of the wiring film 120, and a portion of the conductor film 121 is exposed to touch the skin. A contact potential with the skin can be reduced by using a material containing silver (Ag) or silver chloride (AgCl) as a main component for the conductor film 121.

Although the electrodes 160 are formed as much as the number required for measurement, the number of wires does not increase. Accordingly, as illustrated in FIG. 14, the selection circuit 132 is disposed for each of the electrodes 160.

Figure 15:
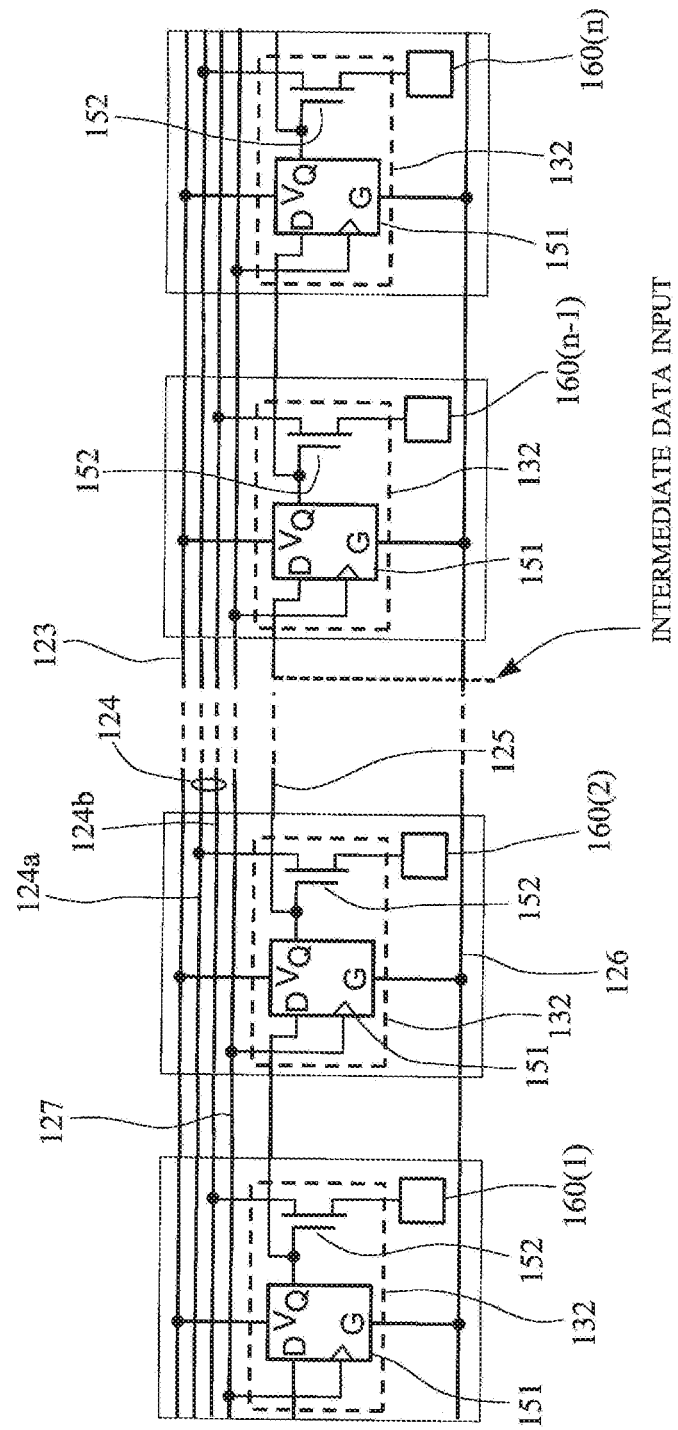
FIG. 15 is a circuit diagram illustrating a specific configuration example of the block diagram in FIG. 14.

Referring to the circuit diagram in FIG. 15, in the seventh embodiment, the selection circuit 132 also includes the latch circuit 151 and the semiconductor switch 152 that is turned on and off by an output of the latch circuit 151. In this example, a MOSFET is used as the semiconductor switch 152. Accordingly, herein, the semiconductor switch will be referred to as the MOSFET. In addition, a flip-flop circuit is used as the latch circuit 151.

Signals of ECG, EMG, or EEG are weak. Accordingly, it is preferable that the signals are read using a balanced line (differential line). The analog line 124 has two lines 124a and 124b, and turns on the selection circuits 132 at any two desired positions. In the present embodiment, a clock line 127 is wired separately from the analog line 124.

The electrode 160 is connected to the source of the MOSFET 152. The drain of the MOSFET 152 is connected to the analog line 124. However, in this example, the odd number is connected to the analog line 124b side, and the even number is connected to the analog line 124a side.

In order to turn on the selection circuits 132 at any two desired positions, a signal may be input to the leading data line 125 to turn on any two desired positions. Alternatively, the above-described preset circuit or reset circuit may be used the selection circuits 132 to set the selection circuits 132 to be shifted by an input of the clock from the clock line 127. Furthermore, data may be input from an intermediate portion of the data line 125. In this manner, it is possible to select any desired one location in front of the intermediate portion and any desired one location subsequent thereto.

Figure 16:
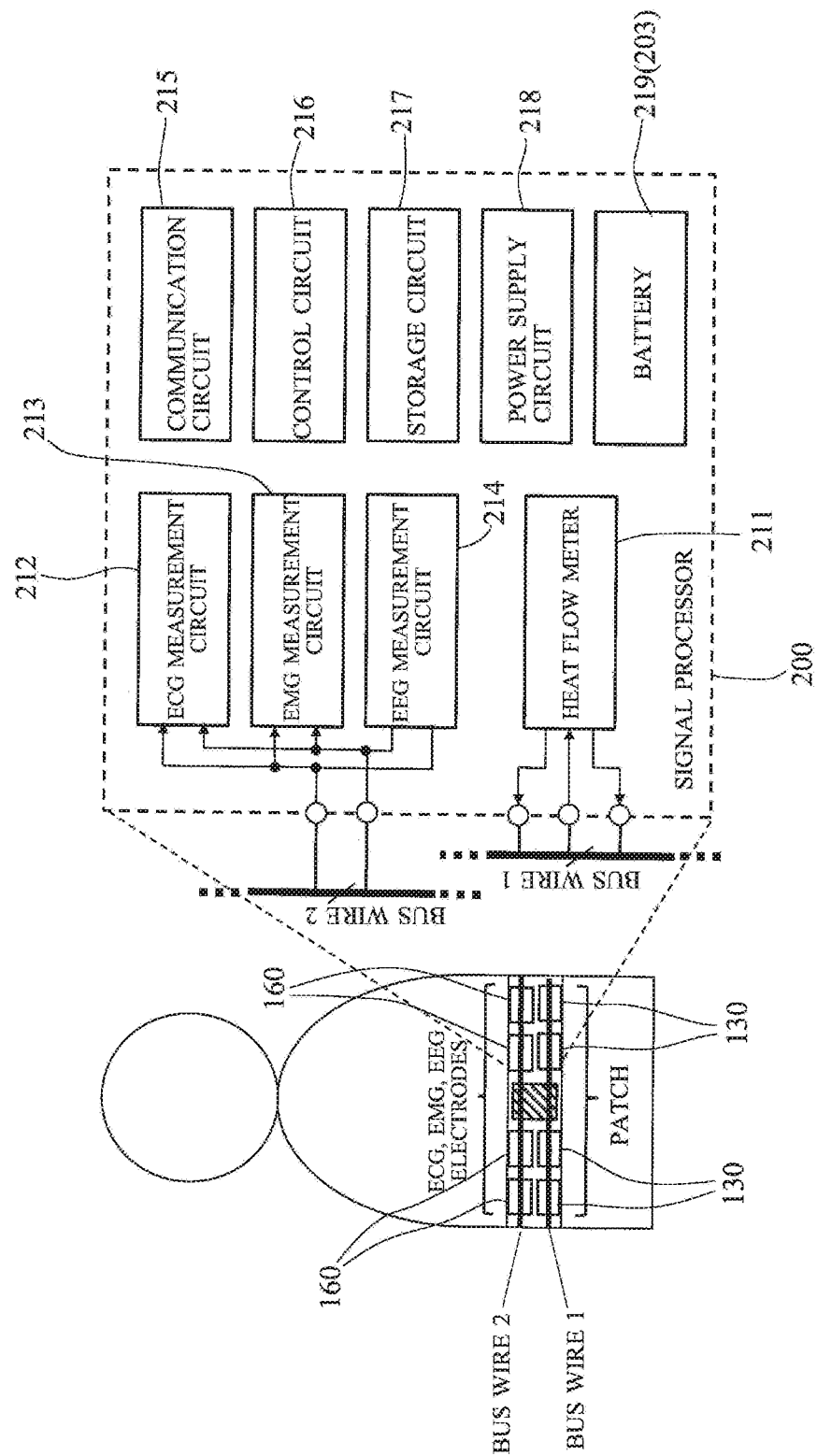
FIG. 16 is a schematic view for describing an aspect in which a core body temperature and ECG, EMG, and EEG are simultaneously measured as an eighth embodiment according to the present invention.

Next, referring to FIG. 16, as an eighth embodiment, an aspect will be described in which the core body temperature, ECG, EMG, and EEG are simultaneously measured.

In this case, two bus wires such as the temperature measuring bus wire 1 having the thermometer 131 described above with reference to FIG. 7 and a signal detecting bus wire 2 having the electrode 160 for detecting a weak signal such as electrocardiogram described above with reference to FIG. 15 are used.

The temperature measuring bus wire 1 is connected to a heat flow meter 211 inside the signal processor 200 via the connection terminal 410 on the wiring film side and the connection terminal 420 on the signal processor side as described above. The heat flow meter 211 sequentially reads the temperature measurement signals from the thermometers 131 and 141 disposed in the respective patches 100 via the bus wire 1.

For example, the electrode 160 disposed in the signal detecting bus wire 2 is disposed around the chest close to the heart for ECG measurement, is disposed around the muscle for EMG measurement, or is disposed on the head for EEG measurement.

The electrodes 160 are connected to an ECG measurement circuit 212, an EMG measurement circuit 213, and an EEG measurement circuit 214 inside the signal processor 200 via the analog lines 124a and 124b. In each of the measurement circuits, an optimum filter or gain is applied to a detection target signal.

According to the eighth embodiment, the core body temperature, and biological potentials of ECG, EMG, and EEG can be simultaneously measured. In addition to the heat flow meter and various measurement circuits, the signal processor 200 has a communication circuit 215 for communicating with an external device (for example, a personal computer), a control circuit 216 for controlling calculation and each unit, a storage circuit 217, a power supply circuit 218, and a battery 219.

Figure 17:
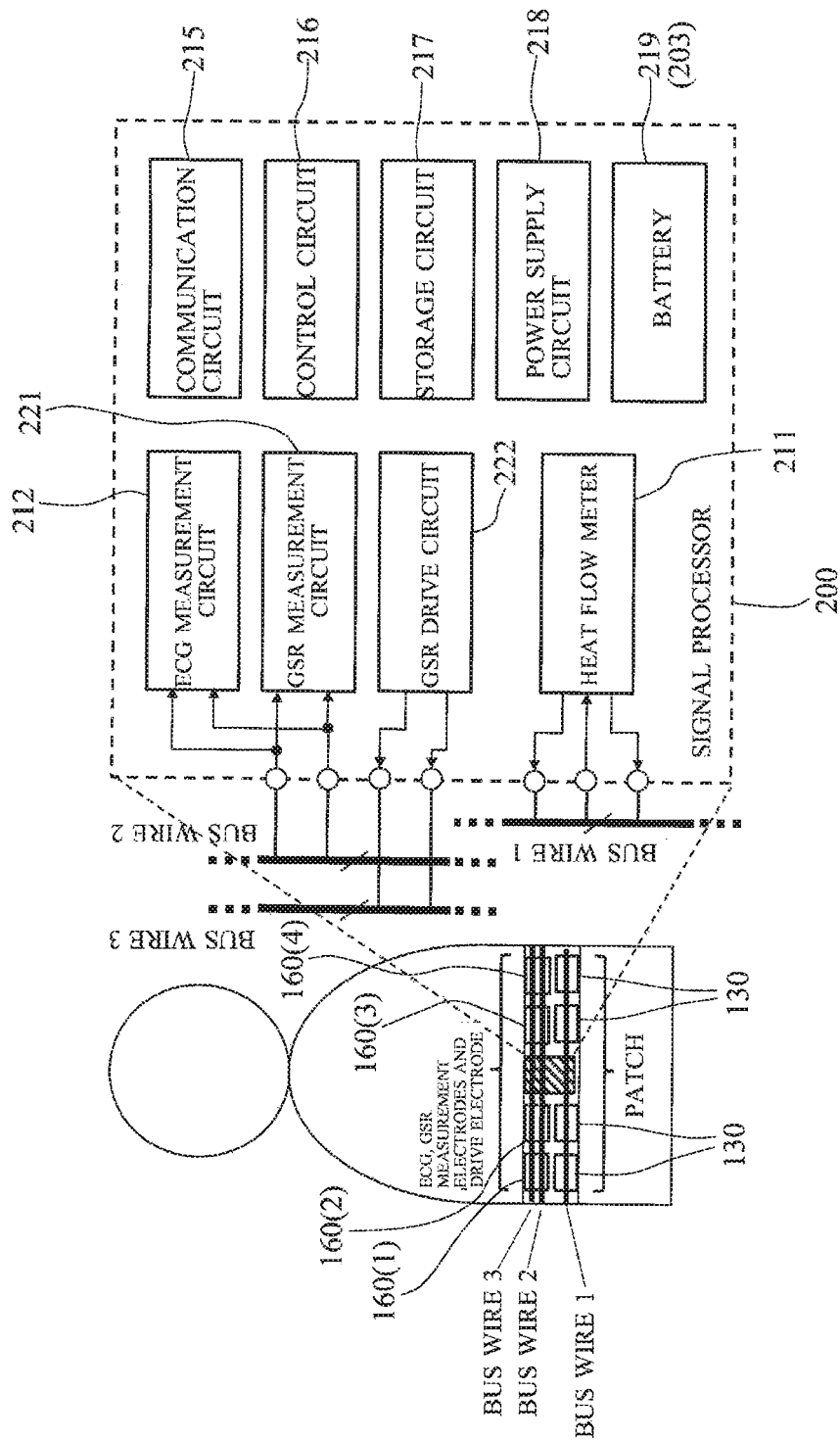
FIG. 17 is a schematic view for describing an aspect in which a core body temperature and GSR are simultaneously measured as a ninth embodiment according to the present invention.

Next, referring to FIG. 17, as a ninth embodiment, an aspect will be described in which the core body temperature, ECG, and GSR are simultaneously measured.

In this case, the signal processor 200 further includes a GSR measurement circuit 221 and a GSR drive circuit 222. Although the EMG measurement circuit 213 and the EEG measurement circuit 214 which are described above are not illustrated in FIG. 17, the measurement circuits may be included in the signal processor 200.

In the present embodiment, in the GSR measurement, preferably, according to a four-terminal method, a voltage is applied to the human body via two electrodes, and a current flowing in the human body is detected by the other two electrodes. Accordingly, in addition to the signal detecting bus wire 2, the voltage applying bus wire 3 is used. The bus wire 3 may have the same configuration as the bus wire 2.

For example, as illustrated in the drawing, four electrodes 160(1), 160(2), 160(3), and 160(4) are aligned around the abdomen. In measuring GSR, the two outer electrodes 160(1) and 160(4) are connected to the GSR drive circuit 222 via the bus wire 3, and the two inner electrodes 160(2) and 160(3) are connected to the GSR measurement circuit 221 via the bus wire 2.

In this way, the core body temperature, ECG, and GSR can be simultaneously measured. However, the characteristics of the present invention is that the electrodes at any two desired locations can be selected. When the number of electrodes is denoted by n, any desired number of electrode can be placed. For example, many measurement electrodes and drive electrodes can be placed around the body so that the body can be measured in slices (EIT measurement).

Figure 18:
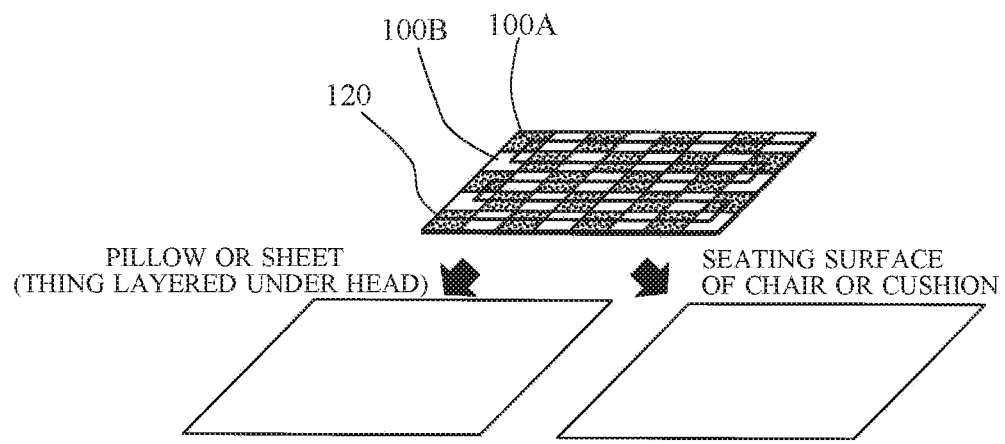
FIG. 18 is a schematic view for describing an aspect suitable for circadian rhythm measurement as a tenth embodiment according to the present invention.
Figure 19:
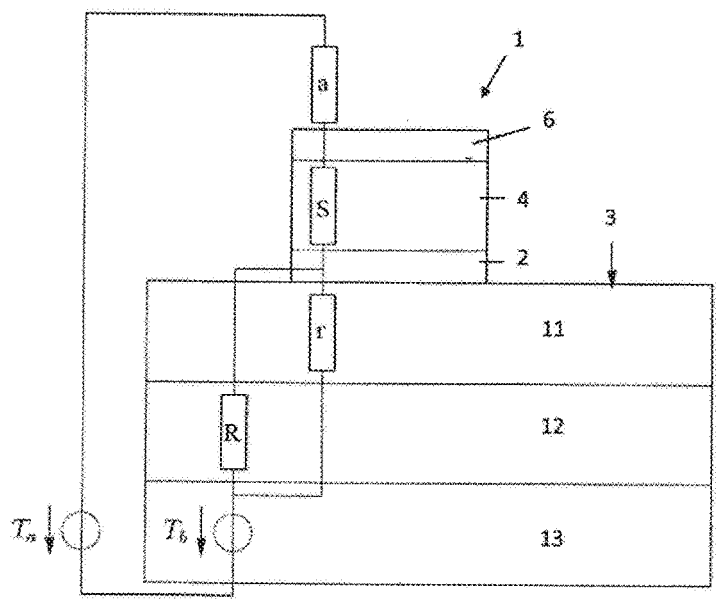
FIG. 19 is a schematic view illustrating an SHF method as a first technique in the related art.
Figure 20:
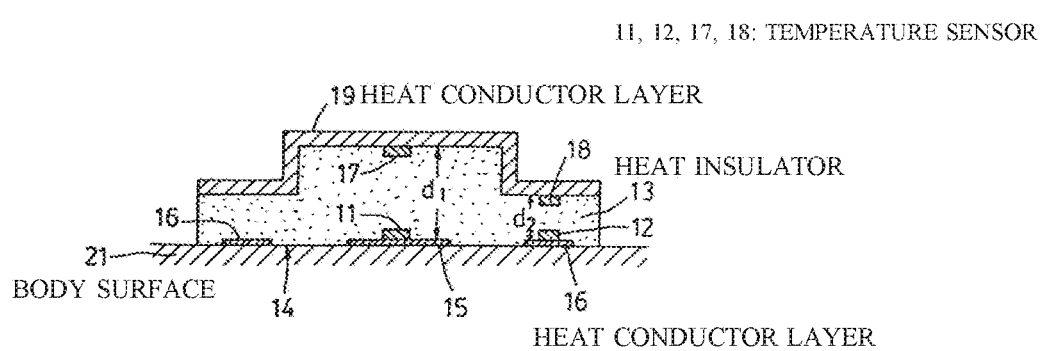
FIG. 20 is a schematic view illustrating a DHF method as a second technique in the related art.
Figure 21:
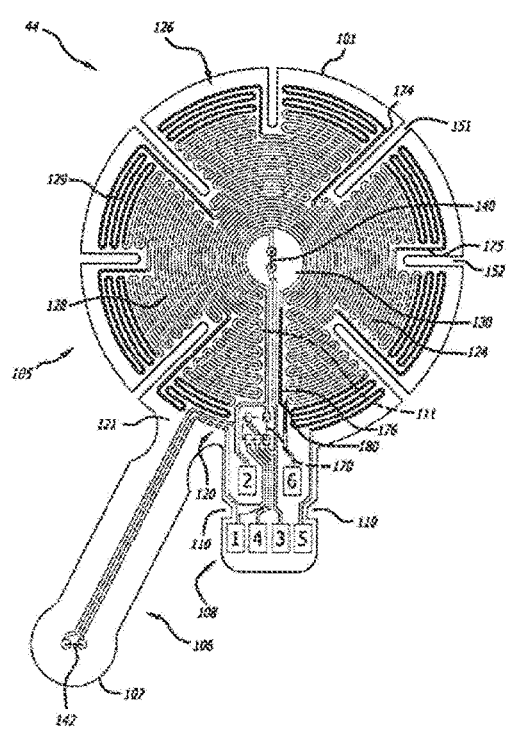
FIG. 21 is a schematic view illustrating a ZHF method as a third technique in the related art.

Next, referring to FIG. 18, an aspect suitable for measuring circadian rhythm (circadian rhythm) will be described as a tenth embodiment.

The present embodiment adopts two types of patches (here, patches 100A and 100B) having different thicknesses of the heat insulators 111 and 112 described above in FIG. 5 which can measure the core body temperature by using the DHF method.

In FIG. 5 described above, a configuration has been described in which the two types of patches 100A and 100B are alternately aligned and connected in one line state via the bus wire (wiring film) 120. However, in the tenth embodiment, the patches 100A and 100B are alternately disposed in a checkered pattern to form a planar DHF sensor.

As described above, the respective patches 100A and 100B have the selection circuits 132 and 142. Accordingly, the patches 100A and 100B are connected in series by a single bus wire 120. In this manner, it is possible to easily read the temperature measurement signal.

The DHF sensor including the patches 100A and 100B is used for circadian rhythm measurement, and is placed in things under the head at bedtime, such as a pillow, a sheets, a mattress, and a sleeping mat that come. Furthermore, the DHF sensor is applicable to things under the lower half body at daytime, such as a chair seating surface, a cushions, and a sofa.

For example, several tens of 20 mm square patches may be aligned so that the pillow or the chair seating surface can be covered. In this manner, even if a position of the head moves due to turning at bedtime or a position of the buttocks or the lower half body moves due to re-sitting on the chair, the core body temperature can be measured using the patch disposed somewhere.

For example, at bedtime, in a case where the head and the pillow are in contact with each other in an area of 60 mm×30 mm, the head is in contact with 2×1 or more patches. In a case where the patches 100A and 100B are alternately aligned, one or more patches 100A and one or more patches 100B can be in contact with the head. Accordingly, an absolute value of the core body temperature Tcore can be obtained from a principle of the DHF method.

In a case of an infant is a measurement target, such as application to a case where there is relatively little individual difference in the subcutaneous thickness, or an application to a case where the absolute value is not important, the SHF method may be used so that a statistical average value can be used as the subcutaneous thickness. In this case, as the patch, only one type may be used.

According to the tenth embodiment, fluctuations in the core body temperature of the measurement target (circadian rhythm) can be measured from bedtime to daytime. In addition, data is transmitted from the sensor to the server via the terminal. In this manner, the core body temperature can be obtained at home or at work, and comprehensive determination can be made, based on a change in the core body temperature throughout one day or for several days.

According to the present invention, the following advantageous effects are achieved in terms of portability, biocompatibility, robustness, reliability, operability, maintainability, cost, and comprehensive determination.

(a) Portability: The patch can have the thickness of approximately several mm and the weight of approximately several grams. The signal processor can be as flexible as a plaster, and can have the size of approximately 15 mm×40 mm×5 mm and the weight of approximately 10 grams. Accordingly, a user's burden and discomfort can be reduced. In addition, data can be wirelessly shared with the cloud.

(b) Biocompatibility: The insulating film containing silicon as the main component is used for the portion which comes into contact with the skin. Accordingly, influence of rashes can be minimized.

(c) Robustness: The temperature between Tsub and Tsk can be raised to several degrees Celsius by using the heat insulator formed of a foam material. High sensitivity can be achieved by the thermometer using a high resistance temperature coefficient (several %/° C. to several tens %/° C.) such as the NTC thermistor. In this manner, and a high S/N ratio can be maintained even if noise is input. In addition, a material such as silicone having a flexible structure using a thin film and having adhesiveness is used on the skin surface. Accordingly, there is little positional displacement even if the body moves.

(d) Reliability: The number of wires can be significantly reduced by using the selection circuit. For example, in a case where four core body temperatures are measured using a belt type, 2 to 4 thermometers are required for one patch. Accordingly, 8 to 16 thermistors are required in total. In the related art, 16 to 32 wires have to be laid around. However, according to the present invention, only four wires and three contact portions are required. As described above, the number of wires and the number of contacts are reduced. In this manner, an area for one wire or a contact can be increased. Therefore, together with the reduced number, the reliability of electrical connection can be significantly improved.

(e) Operability: The contact portions using the magnet can be positioned in a self-aligned manner when the case of the signal processor is moved closer. Therefore, the patch can be intuitively mounted even by a user who uses the patch for the first time. The signal processor is wirelessly controlled. For the control, an algorithm or computer power inside the terminal or the cloud can be used. Therefore, a parameter can be set for each user without user's awareness.

(f) Maintainability: The insulating film containing silicon as the component and the conductor film using a precious metal are used. In this manner, the patch unit, the belt provided with the patch, and the garment can be washed as they are. Therefore, sweat components and dirt such as oil and fat on the body can be removed. As the circuit, only the thermometer and the selection circuit are used, and no expensive component is used. Therefore, it is possible to provide a replacing system when being dirty.

(g) Cost: The patch can be connected in a single stroke drawing form by using the belt-shaped or sheet-shaped wiring film made of the insulating film or the conductor film. Therefore, the number of joints can be reduced, and the patch can be easily manufactured using an automatic machine.

(h) Comprehensive Determination: The system has the measurement means for measuring the body temperature, the environmental temperature, ECG, and GSR. Based on the temperature information, the system recognizes that the user is in a high temperature environment or in a low temperature environment. Based on ECG or GSR, the system recognizes that the user is placed in an exercise or in a stress environment. Based on comprehensive determination including the autonomic nervous state, the system can provide the user's physical condition information for suitable persons such as the user, an administrator, and other health care workers.

REFERENCE SIGNS LIST

100: patch
111,112: heat insulator
120: wiring film
121: conductor film
122: insulating film
123: power supply line
124 (124a, 124b): analog line
125: data line
126: ground (GND) line
130,140: temperature measurement circuit
131,141: thermometer
132, 142: selection circuit
151: latch circuit
152: semiconductor switch (MOSFET)
160: electrode
200: signal processor
211: heat flow meter
212: EDG measurement circuit
213: EMG measurement circuit
214: EEG measurement circuit
215: communication circuit
216: control circuit
217: storage circuit
218: power supply circuit
219: power supply (built-in battery)
221: GSR measurement circuit
222: GSR drive circuit
410 (411, 412, 413): connection terminal on wiring film side
420 (421, 422, 423): connection terminal on signal processor side
BS: body surface
Ith: heat flow (heat flux)
Rthbody: internal heat resistance
Tsk: body surface temperature
Tsub: temperature of layered surface
Tcore: core body temperature

The invention claimed is:

1. A biological data measurement device comprising:
a patch including
a first heat insulator disposed on a body surface of a living body which is a measurement object,
a second heat insulator layered on the first heat insulator,
a belt-shaped conductor film that is wired over at least a layered surface between the first heat insulator and the second heat insulator from a bottom surface of the first heat insulator on the body surface side,
a first temperature measurement circuit including a first thermometer, and disposed on the conductor film on the bottom surface side of the first heat insulator, and
a second temperature measurement circuit including a second thermometer, and disposed on the conductor film in the layered surface.

2. The biological data measurement device according to claim 1,
wherein both surfaces of the conductor film are covered with an electrically insulating film except for an electrical connection portion connected to each of the temperature measurement circuits.

3. The biological data measurement device according to claim 1,
wherein a biocompatible skin contact layer including a wiring portion of the conductor film is disposed on the bottom surface of the first heat insulator on the body surface side.

4. The biological data measurement device according to claim 1,
wherein the first temperature measurement circuit and the second temperature measurement circuit are connected in series to a bus wire included in the conductor film, and each of the temperature measurement circuits is equipped with a selection circuit that turns on and off an output of a temperature signal measured by each of the first and second thermometers.

5. The biological data measurement device according to claim 4,
wherein the selection circuit selectively outputs the temperature signal measured by the first thermometer and the temperature signal measured by the second thermometer at a predetermined timing.

6. The biological data measurement device according to claim 4,
wherein the selection circuit includes a latch circuit that is operated by a selection signal from an outside, and a semiconductor switch that is turned on and off by an output of the latch circuit, the bus wire includes an analog line for reading the temperature signal, a power supply line, and a ground line, and each of the first and second thermometers is connected between the analog line and the ground line via the semiconductor switch.

7. The biological data measurement device according to claim 6,
wherein a plurality of the patches are provided, and
wherein the respective patches are connected in series via the conductor film including the bus wire.

8. The biological data measurement device according to claim 7,
wherein the number of the patches is an even number, and thicknesses of the heat insulators are different from each other between an odd-numbered first patch and an even-numbered second patch.

9. The biological data measurement device according to claim 4,
wherein a plurality of the patches are supported by a mounting belt for a human body in a state where the patches are connected in series via the conductor film including the bus wire.

10. The biological data measurement device according to claim 4,
wherein a plurality of patches are disposed on a garment in a state where the patches are connected in series via the conductor film including the bus wire.

11. The biological data measurement device according to claim 7,
wherein the conductor film has a contact portion including a first connection terminal connected to the analog line, a second connection terminal connected to the power supply line, and a third connection terminal connected to the ground line.

12. The biological data measurement device according to claim 11,
wherein the contact portion is disposed in the conductor film existing between the patches.

13. The biological data measurement device according to claim 11,
wherein the contact portion is disposed on an upper surface of the second heat insulator of the patch.

14. The biological data measurement device according to claim 11, further comprising:
a signal processor that can be electrically and mechanically attached to and detached from the contact portion, that provides the latch circuit with a control clock for a power supply and a latch operation, and that performs predetermined processing on a temperature signal by collecting the temperature signal from each of the thermometers.

15. The biological data measurement device according to claim 14,
wherein the signal processor includes an arithmetic unit that obtains a heat flow Ith from $(Tsk-Tsub)/Rthins$, when a body surface temperature measured by the first thermometer is denoted by Tsk, a temperature of the layered surface measured by the second thermometer is denoted by Tsub, heat resistance of a first heat insulating layer is denoted by Rthins, and a heat flow that flows perpendicular to the body surface is denoted by Ith.

16. The biological data measurement device according to claim 15,
wherein the number of the patches is an even number, and thicknesses of the heat insulators are different from each other between an odd-numbered first patch and an even-numbered second patch, and
wherein when a body surface temperature measured by the first thermometer of the first patch is denoted by Tsk1, a heat flow that flows perpendicular to the body surface in a temperature measurement portion is denoted by Ith1, a body surface temperature measured by the first thermometer of the second patch is denoted by Tsk2, a heat flow that flows perpendicular to the body surface is denoted by Ith2, and internal heat resistance from a core tissue of the living body to the body surface is denoted by Rthbody, the arithmetic unit calculates Rthbody from $(Tsk2-Tsk1)/(Ith1-Ith2)$, and thereafter, obtains a core body temperature Tcore of the living body from $(Ith1 \times Rthbody+Tsk1)$ or $(Ith2 \times Rthbody+Tsk2)$.

* * * * *